(12) United States Patent
Fedurco et al.

(10) Patent No.: US 9,617,372 B2
(45) Date of Patent: Apr. 11, 2017

(54) SULPHUR-COMPRISING POLYAROMATIC POLYAMINE THAT CAN BE USED IN THE SYNTHESIS OF POLYUREA

(71) Applicants: COMPAGNIE GENERALE DES ETABLISSEMENTS MICHELIN, Clermont-Ferrand (FR); Michelin Recherche et Technique S.A., Granges-Paccot (CH)

(72) Inventors: Milan Fedurco, Clermont-Ferrand (FR); Marco Ribezzo, Clermont-Ferrand (FR)

(73) Assignees: Compagnie Generale Des Etablissements Michelin, Clermont-Ferrand (FR); Michelin Recherche Et Technique S.A., Granges-Paccot (CH)

( * ) Notice: Subject to any disclaimer, the term of this patent is extended or adjusted under 35 U.S.C. 154(b) by 0 days.

(21) Appl. No.: 14/438,396

(22) PCT Filed: Oct. 16, 2013

(86) PCT No.: PCT/EP2013/071619
§ 371 (c)(1),
(2) Date: Apr. 24, 2015

(87) PCT Pub. No.: WO2014/063968
PCT Pub. Date: May 1, 2014

(65) Prior Publication Data
US 2015/0274878 A1 Oct. 1, 2015

(30) Foreign Application Priority Data
Oct. 24, 2012 (FR) ...................................... 12 60101

(51) Int. Cl.
*C08G 18/32* (2006.01)
*C07C 323/36* (2006.01)
(Continued)

(52) U.S. Cl.
CPC ........ *C08G 18/3243* (2013.01); *C07C 323/36* (2013.01); *C08G 18/3868* (2013.01);
(Continued)

(58) Field of Classification Search
CPC .... C07C 323/34; C07C 323/35; C07C 323/36
(Continued)

(56) References Cited

U.S. PATENT DOCUMENTS 4,757,119 A * 7/1988 Wiggins ............... C08G 59/504
525/504
5,124,426 A * 6/1992 Primeaux, II ...... C08G 18/3868
528/60
(Continued)

FOREIGN PATENT DOCUMENTS

CN 102625815 A 8/2012
WO 2008/051229 A1 5/2008

OTHER PUBLICATIONS

Fedurco, U.S. Appl. No. 14/438,382, filed Oct. 16, 2013.
(Continued)

*Primary Examiner* — Mike M Dollinger
(74) *Attorney, Agent, or Firm* — Fitzpatrick, Cella, Harper & Scinto

(57) ABSTRACT

A sulphur-comprising polyaromatic polyamine compound can be used as a monomer or prepolymer, when n is different from zero, in the synthesis of polyurea. The compound corresponds to the formula (I):

(Continued)

(I)

in which X represents the string:

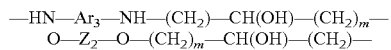

and in which n represents an integer equal to zero or different from zero; m, which are identical or different, represent an integer within a range from 1 to 10; $Z_1$ and $Z_2$, which are identical or different, represent a divalent bonding group comprising from 1 to 30 carbon atoms; and $Ar_1$, $Ar_2$ and $Ar_3$, which are identical or different, each represent a phenylene group, at least one of these phenylene groups bearing one, two, three or four groups of formula —$S_x$—R in which "x" is an integer from 1 to 8 and R represents hydrogen or a hydrocarbon group which can comprise a heteroatom and which comprises from 1 to 10 carbon atoms.

19 Claims, 10 Drawing Sheets

(51) Int. Cl.
*C08G 18/64* (2006.01)
*C08G 18/80* (2006.01)
*C08G 18/38* (2006.01)
*C09J 175/02* (2006.01)
*C08G 18/76* (2006.01)

(52) U.S. Cl.
CPC ....... *C08G 18/643* (2013.01); *C08G 18/7664* (2013.01); *C08G 18/80* (2013.01); *C08G 18/8074* (2013.01); *C09J 175/02* (2013.01); *C07C 2101/14* (2013.01)

(58) Field of Classification Search
USPC .......................................................... 525/452
See application file for complete search history.

(56) References Cited

U.S. PATENT DOCUMENTS

| | | | |
|---|---|---|---|
| 5,534,036 A * | 7/1996 | Junino | A61K 8/411 |
| | | | 8/406 |
| 6,723,821 B2 | 4/2004 | Smith | 528/62 |
| 7,432,399 B2 * | 10/2008 | Verborgt | C07C 217/28 |
| | | | 564/305 |
| 2010/0021676 A1 | 1/2010 | Laubry | 428/63 |
| 2010/0210745 A1 | 8/2010 | McDaniel et al. | 521/55 |
| 2011/0039982 A1 | 2/2011 | Hefner, Jr. et al. | 523/400 |
| 2012/0097194 A1 | 4/2012 | McDaniel et al. | 134/26 |
| 2012/0157620 A1 | 6/2012 | Nagy et al. | 524/612 |
| 2013/0079485 A1 | 3/2013 | Cai et al. | 528/55 |
| 2014/0315898 A1 * | 10/2014 | Koehler | A01N 41/10 |
| | | | 514/227.2 |

OTHER PUBLICATIONS

International Search Report dated Jan. 20, 2014, issued by EPO in connection with International Application No. PCT/EP2013/071619.

* cited by examiner (II)

X:

(II-A)

(II-B)

(II-C)

(III-A)

(III-B)

(III-C)

(III-D)

Polyurea1

Monomer C1

170°C

Monomer D

Polyurea 1

Polyurea 2

SULPHUR-COMPRISING POLYAROMATIC POLYAMINE THAT CAN BE USED IN THE SYNTHESIS OF POLYUREA

I. FIELD OF THE INVENTION

The present invention relates to the monomers or prepolymers which can be used in the synthesis of polyureas (polymers comprising urea units) intended in particular for adhesive systems for the adhesive bonding of metal or glass to rubber, especially in metal/rubber composites intended for articles made of rubber, such as tyres.

It more particularly relates to the above monomers or prepolymers of the sulphur-comprising polyaromatic polyamine type.

II. STATE OF THE ART

Metal/rubber composites, in particular for tyres, are well known. They are generally composed of a matrix made of unsaturated rubber, generally diene rubber, which can be crosslinked with sulphur, comprising metal reinforcing elements (or "reinforcers") such as threads, films or cords made of carbon steel.

As they are subjected to very high stresses during the rolling of the tyres, in particular to repeated actions of compression, bending or variation in curvature, these composites must, in a known way, satisfy a large number of sometimes contradictory technical criteria, such as uniformity, flexibility, endurance in bending or compression, tensile strength, wear resistance and corrosion resistance, and must maintain this performance at a very high level for as long as possible.

It is easily understood that the adhesive interphase between rubber and metal plays a dominating role in the persistence of this performance. The conventional process for connecting the rubber compositions to carbon steel consists in coating the surface of the steel with brass (copper/zinc alloy), the bonding between the steel and the rubber matrix being provided by sulphurization of the brass during the vulcanization or curing of the rubber. In order to improve the adhesion, use is moreover generally made, in these rubber compositions, as adhesion-promoting additives, of metal, such as cobalt, complexes or organic salts.

In point of fact, it is known that the adhesion between the carbon steel and the rubber matrix is capable of weakening over time as a result of the gradual development of sulphides formed under the effect of the various stresses encountered, in particular mechanical and/or thermal stresses, it being possible for the above decomposition process to be accelerated in the presence of moisture.

Moreover, the use of cobalt salts renders the rubber compositions more sensitive to oxidation and to ageing, and significantly increases the cost thereof, not to mention that it is desirable to eliminate, in the long run, the use of such cobalt salts in rubber compositions due to recent developments in European regulations relating to metal salts of this type.

For all the reasons set out above, manufacturers of metal/rubber composites, in particular tyre manufacturers, are on the lookout for novel adhesive solutions in order to adhesively bond metal reinforcers to rubber compositions, while overcoming, at least in part, the abovementioned disadvantages.

III. BRIEF DESCRIPTION OF THE INVENTION

In point of fact, during their research studies, the Applicant Companies have found a novel polyamine compound, more particularly a specific sulphur-comprising polyaromatic polyamine, which can be used as monomer or (when n is other than zero in the formula I below) as prepolymer in the synthesis of a polyurea which meets such an objective.

According to the invention, the said sulphur-comprising polyaromatic polyamine corresponds to the formula (I):

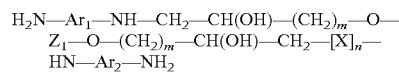

in which X represents the string:

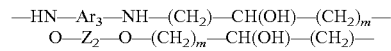

and in which:
  the "n" symbol represents an integer equal to zero or different from zero;
  the "m" symbols, which are identical or different, represent an integer within a range from 1 to 10;
  the $Z_1$ and $Z_2$ symbols, which are identical or different, represent a divalent bonding group comprising from 1 to 30 carbon atoms;
  $Ar_1$, $Ar_2$ and $Ar_3$, which are identical or different, represent a phenylene group, one at least of these phenylene groups bearing one, two, three or four groups of formula —$S_x$—R in which "x" is an integer from 1 to 8 and R represents hydrogen or a hydrocarbon group which can comprise a heteroatom and which comprises from 1 to 10 carbon atoms.

By virtue of this polyamine in accordance with the invention, it is possible to prepare a polyurea which, used as adhesion primer, for example on metal reinforcers, gives such reinforcers the major advantage of being able subsequently to be adhesively bonded to unsaturated rubber matrices using simple textile adhesives, such as "RFL" (resorcinol/formaldehyde latex) adhesives or other equivalent adhesive compositions, or also directly (that is to say, without employing such adhesives) to these unsaturated rubber matrices when the latter comprise appropriate functionalized unsaturated elastomers, such as epoxidized elastomers.

The invention also relates to the use of a polyamine compound in accordance with the invention in the manufacture of a polyurea and also to any polyurea resulting from at least one polyamine compound in accordance with the invention.

The invention also relates to any process for the synthesis of a polyurea by polycondensation of at least one compound in accordance with the invention with a polyisocyanate compound.

BRIEF DESCRIPTION OF THE FIGURES

The invention and its advantages will be easily understood in the light of the detailed description and implementational examples which follow, and also of the figures relating to these examples, which represent or schematize.

IV. DETAILED DESCRIPTION OF THE INVENTION

Figure 1:
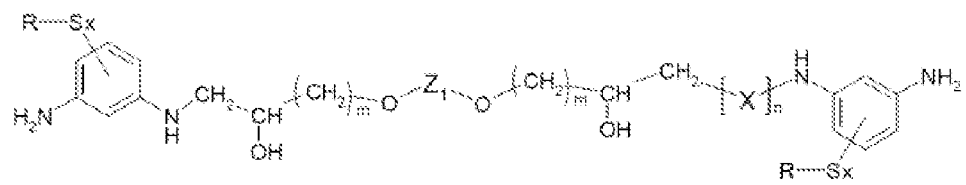
FIG. 1—an example of sulphur-comprising polyaromatic polyamine, the sub-unit of general formula (I) above of which corresponds to the specific formula (II) in which, on each phenylene group, the amino (NH and/or $NH_2$) groups are in the meta position with respect to one another.
Figure 1:
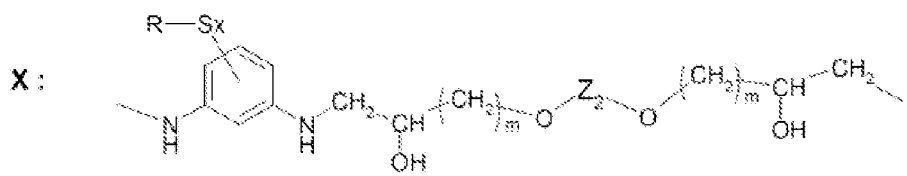

It should be remembered first of all that a polyurea is a polymer (by definition any homopolymer or copolymer, in particular block copolymer) comprising a plurality of urea (—NH—CO—NH—) bonds resulting, in a known way, from the addition reaction of a polyamine having at least two primary amine functional groups with a polyisocyanate (compound bearing at least two isocyanate —NCO functional groups), in particular with a diisocyanate in the case of a polyurea of the linear type.

The polyaromatic polyamine compound of the invention thus has the essential characteristic of corresponding to the formula (I) below:

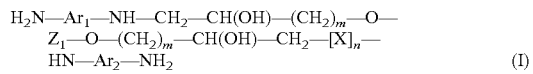

X represents the string:

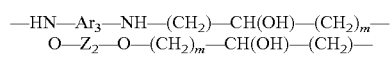

"n" is an integer equal to zero or different from zero;
the "m" symbols, which are identical or different, represent an integer within a range from 1 to 10, preferably from 1 to 5;

the $Z_1$ and $Z_2$ symbols, which are identical or different, represent a divalent bonding group comprising from 1 to 30 carbon atoms;

$Ar_1$, $Ar_2$ and $Ar_3$, which are identical or different, represent a phenylene group, one at least of these phenylene groups bearing one, two or three groups of formula —$S_x$—R in which "x" is an integer from 1 to 8 and R represents hydrogen or a hydrocarbon group which can comprise a heteroatom and which comprises from 1 to 10 carbon atoms.

"x" is an integer from 1 to 8, preferably from 1 to 4, more preferably equal to 1 or 2 and more particularly equal to 1.

R represents hydrogen or a substituted or unsubstituted hydrocarbon group which comprises from 1 to 10 carbon atoms and which can comprise a heteroatom, such as S, O or N. Preferably, R is an aliphatic group and more preferably an alkyl group. More preferably still, R is an alkyl having from 1 to 5 carbon atoms, it being possible for this alkyl to be substituted or unsubstituted; more particularly, R represents a methyl or an ethyl and more particularly still a methyl.

In the specific cases where, in the —$S_x$—R group of the sub-unit (I) above, R represents hydrogen, a person skilled in the art will understand that, during the synthesis of the polyaromatic polyamine of the invention, by reaction of a starting diamine (for example Monomer A below) with a diepoxy compound (for example Monomer B below), the thiol —SH group can be protected from any side reaction with this diepoxy compound, in a known way, by an appropriate blocking group known to a person skilled in the art, for example as represented in the formulae below:

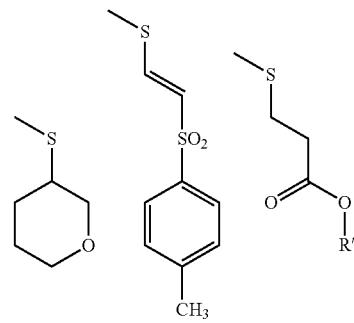

According to a preferred form of the invention, each of the $Ar_1$, $Ar_2$ and $Ar_3$ groups, which are identical or different, bears one, two, three or four groups of formula —$S_x$—R, in particular two SR groups (x equal to 1), in which R is an alkyl having from 1 to 5 carbon atoms, R being more particularly a methyl or an ethyl and more particularly still a methyl.

According to a more preferred embodiment, $Ar_1$, $Ar_2$ and $Ar_3$, which are identical or different, each bear two —$S_x$—R groups, in particular two SR groups (x equal to 1), in which R is an alkyl having from 1 to 5 carbon atoms, R being more particularly a methyl or an ethyl and more particularly still a methyl. More preferably still, in such a case, the two —SR, in particular —$SCH_3$, groups are in the meta position (or 1,3-position) with respect to one another on each phenylene group Ar.

The numbers "m" can be identical or different from one $(CH_2)_m$ group to another; preferably, each number "m" is equal to 1 or 2 and more preferably equal to 1.

The $Z_1$ and $Z_2$ symbols, which are identical or different, represent a divalent bonding group which is preferably a hydrocarbon group but which can also comprise a heteroatom, such as S, O or N; they comprise from 1 to 30 carbon atoms, preferably from 2 to 20 carbon atoms and more preferably from 2 to 10 carbon atoms.

More preferably, $Z_1$ and $Z_2$ represent an aliphatic group comprising from 2 to 20 carbon atoms or a cycloaliphatic group comprising from 3 to 20 carbon atoms, more preferably still an aliphatic or cycloaliphatic group comprising from 3 to 10 carbon atoms. Mention will in particular be made, among these more preferred groups, of cyclohexane-1,4-dimethylene, of formula:

According to another preferred embodiment, "n" is equal to zero. In such a case, the compound in accordance with the invention of formula (I) thus has the simplified formula which follows:

$$H_2N\text{—}Ar_1\text{—}NH\text{—}CH_2\text{—}CH(OH)\text{—}(CH_2)_m\text{—}O\text{—}Z_1\text{—}O\text{—}(CH_2)_m\text{—}CH(OH)\text{—}CH_2\text{—}HN\text{—}Ar_2\text{—}NH_2.$$

In particular, when "n" is equal to zero and "m" is equal to 1 for each $(CH_2)_m$ group, the compound according to the invention of formula (I) then has the more simplified formula:

$$H_2N\text{—}Ar_1\text{—}NH\text{—}CH_2\text{—}CH(OH)\text{—}CH_2\text{—}O\text{—}Z_1\text{—}O\text{—}CH_2\text{—}CH(OH)\text{—}CH_2\text{—}HN\text{—}Ar_2\text{—}NH_2.$$

According to another preferred embodiment, "n" is equal to 1 or greater than 1; when "n" is greater than 1, it is in particular within a range from 2 to 20, more preferably from 2 to 10 and in preferably from 2 to 5.

The phenylenediamino groups, which are monovalent or divalent as the case may be ($H_2N\text{—}Ar_1\text{—}NH\text{—}$, $\text{—}HN\text{—}Ar_2\text{—}NH_2$ and $\text{—}HN\text{—}Ar_3\text{—}NH\text{—}$), can be identical or different.

On each phenylene group Ar, the two amino groups (as the case may be, either 2 NH groups or one NH group and one $NH_2$ group) can be in the meta, ortho or para position with respect to one another.

According to a preferred embodiment, on each phenylene group Ar, these two amino groups are in the meta position (or 1,3-position) with respect to one another. In other words, in such a case, the sub-unit of general formula (I) thus has, as expanded formula (II), that which was represented in the appended FIG. 1.

In such a preferred form, the monovalent phenylenediamino strings $H_2N\text{—}Ar_1\text{—}NH\text{—}$ and $\text{—}HN\text{—}Ar_2\text{—}NH_2$, which are identical or different, correspond in particular to one of the formulae (III-a), (III-b) and (III-c) which follow:

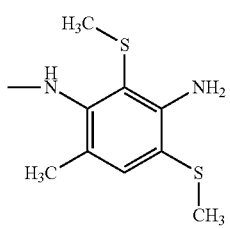

(III-a)

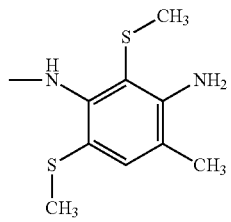

(III-b)

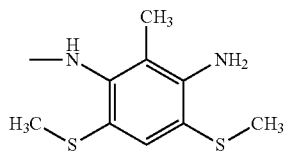

(III-c)

In another preferred form applicable when n is different from zero, this form being more preferably combined with the preferred form which precedes, the divalent phenylenediamino strings $\text{—}HN\text{—}Ar_3\text{—}NH\text{—}$, which are identical or different, for their part correspond to one of the formulae (III-d) and (III-e) which follow:

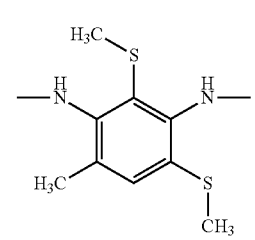

(III-d)

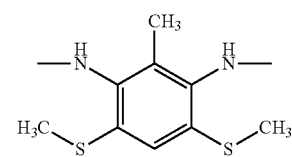

(III-e)

Figure 2A:
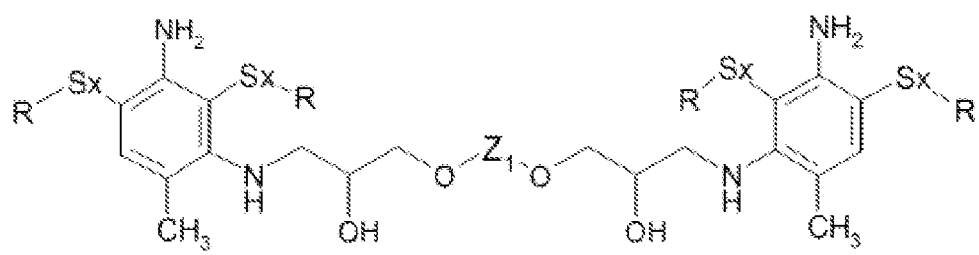
FIGS. 2A, 2B and 2C respectively—three examples of sulphur-comprising polyaromatic polyamines, the sub-unit of specific formula (II) of which corresponds to the more specific formula (II-A), (II-B) or (II-C) in which "m" is equal to 1 for each $(CH_2)_m$ group and "n" is equal to zero.
Figure 2B:
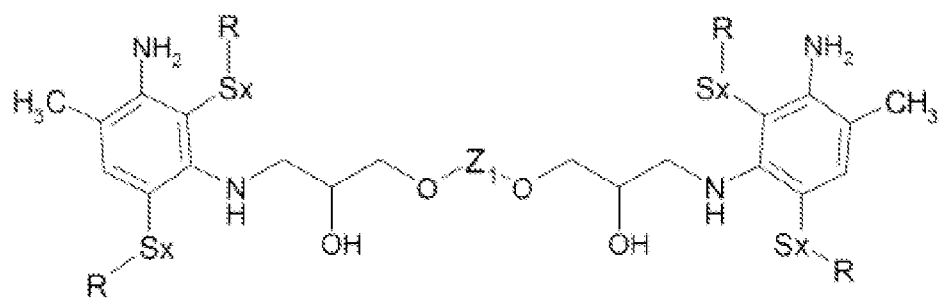
Figure 2C:
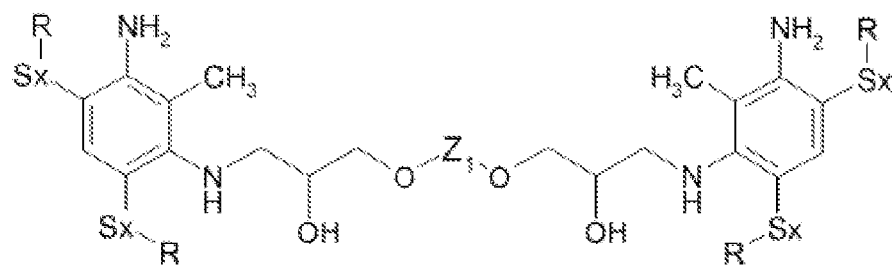

Thus, still in the case where the two amino groups are in the meta position with respect to one another on each phenylene group, that they correspond, on the one hand, to one of the specific formulae (III-a), (III-b), (III-c), (III-d) and (III-e) above and that, on the other hand, according to an even more preferred embodiment, "m" is equal to 1 for each $(CH_2)_m$ group and "n" is equal to 0, then the preceding formula (II) has as more specific formulae the expanded formulae (II-A), (II-B) and (II-C) as represented respectively in the appended FIGS. 2A, 2B and 2C.

Figure 3A:
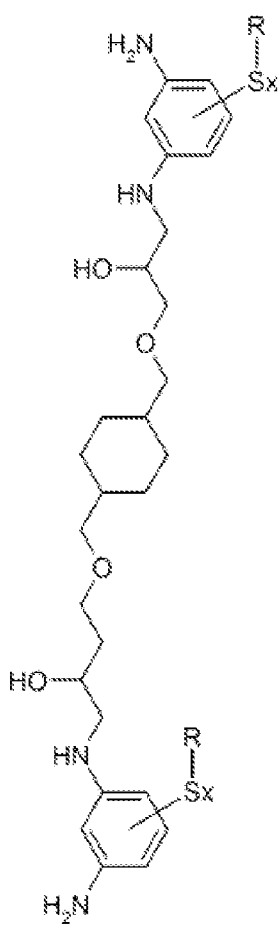
FIGS. 3A and 3B respectively—two examples of sulphur-comprising polyaromatic polyamines, the sub-unit of specific formula (II) of which corresponds to the more specific formula (III-A) or (III-B) in which "m" is equal to 1 for each $(CH_2)_m$ group, $Z_1$ and if appropriate $Z_2$ represent cyclohexane-1,4-dimethylene, and "n" is equal to 0 (III-A) or to 1 (III-B)

Still in the case where the two amino groups are in the meta position with respect to one another on each phenylene group and that, according to a more preferred embodiment, "m" is equal to 1 for each $(CH_2)_m$ group and "n" is equal to 0, $Z_1$ being, for example, cyclohexane-1,4-dimethylene, then the preceding formula (II) has as more specific formula the expanded formula (III-A) as represented in the appended FIG. 3A.

Figure 3B:
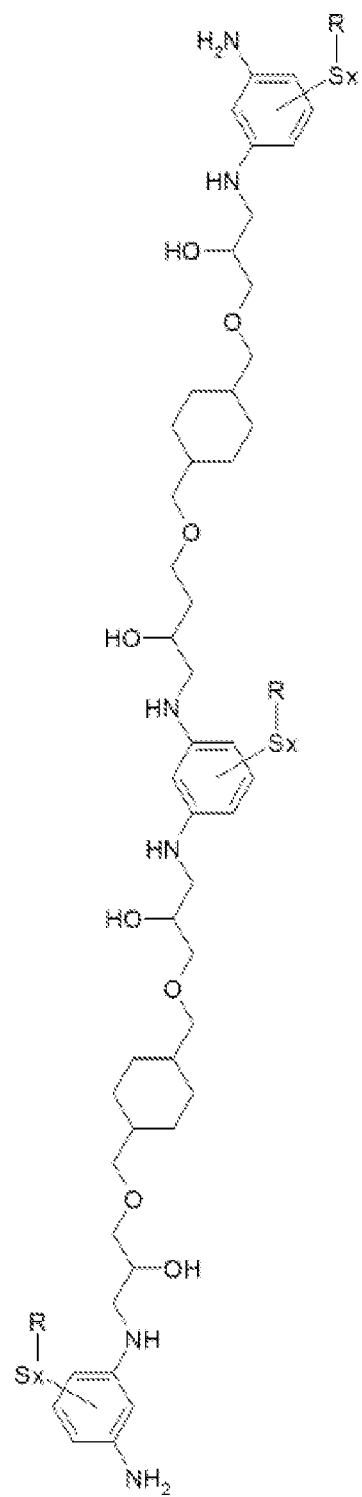
Figure 4A:
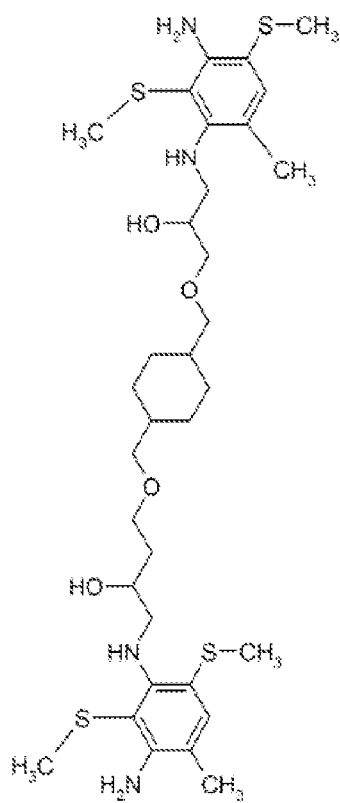
FIGS. 4A and 4B respectively—two examples of sulphur-comprising polyaromatic polyamines, the sub-units of specific formulae (III-A) and (III-B) of which correspond respectively to the more specific formulae (III-C) and (III-D) in which, in addition, each phenylenediamino group corresponds to the specific formula (III-a)
Figure 4B:
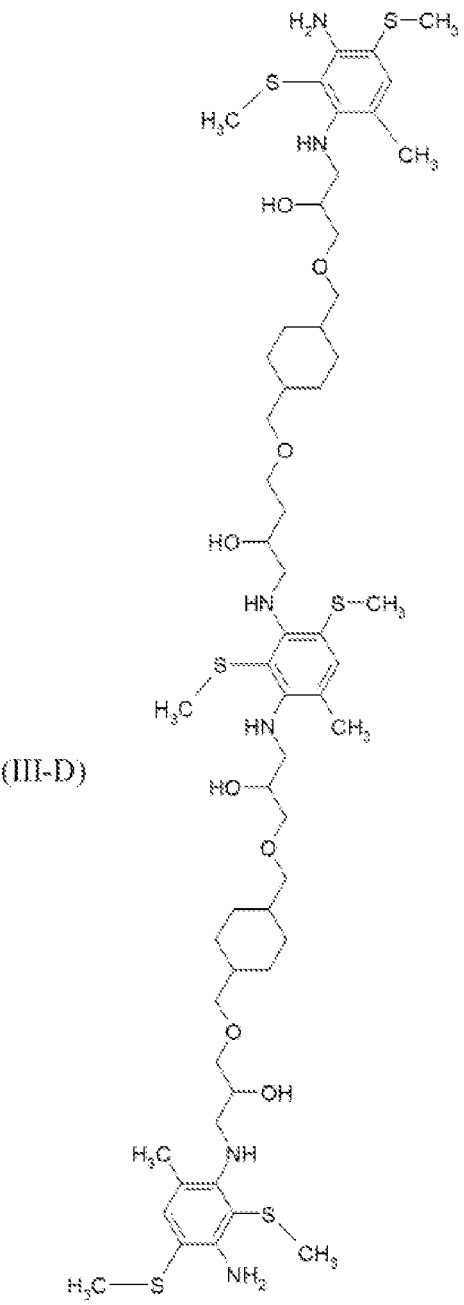

Still in the case where the two amino groups are in the meta position with respect to one another on each phenylene group and that, according to another more preferred embodiment, "m" is equal to 1 for each $(CH_2)_m$ group and "n" is equal to 1, $Z_1$ and $Z_2$ being, for example, cyclohexane-1,4- dimethylene, then the preceding formula (II) has as more specific formula the expanded formula (III-B) as represented in the appended FIG. 3B.

The sulphur-comprising polyaromatic diamine in accordance with the invention described above can preferably be used in the synthesis of a polyurea of the linear type, thus resulting essentially from the addition of this diamine and of a diisocyanate. The diisocyanate which can be used can be aromatic or aliphatic; it can be a monomer, a prepolymer or a quasi-prepolymer, indeed even a polymer.

According to a preferred embodiment, the diisocyanate is selected from the group consisting of the following aromatic compounds: diphenylmethane diisocyanate (abbreviated to "MDI"), toluene diisocyanate ("TDI"), naphthalene diisocyanate ("NDI"), 3,3'-bitoluene diisocyanate ("TODI"), para-phenylene diisocyanate ("PPDI"), their various isomers and the mixtures of these compounds and/or isomers.

More preferably, use is made of an MDI or a TDI, more preferably still of an MDI. All the isomers of MDI (in particular 2,2'-MDI, 2,4'-MDI and 4,4'-MDI) and their mixtures can be used, as well as "polymeric" MDIs (or "PMDIs") comprising oligomers of following formula (with p equal to or greater than 1):

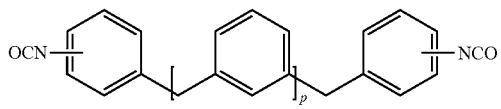

Diisocyanate compounds of the aliphatic type can also be used, such as, for example, 1,4-tetramethylene diisocyanate, 1,6-hexane diisocyanate ("HDI"), 1,4-bis(isocyanatomethyl)cyclohexane, 1,3-bis(isocyanatomethyl)cyclohexane, 1,3-bis(isocyanatomethyl)benzene, 1,4-bis(isocyanatomethyl)benzene, isophorone diisocyanate ("IPDI"), bis(4-isocyanatocyclohexyl)methane diisocyanate ("H12MDI") or 4,4'-dicyclohexylmethane diisocyanate ("H13 MDI").

According to a particularly preferred embodiment, the diisocyanate used is 4,4'-MDI (4,4'-diphenylmethane diisocyanate), having the formula:

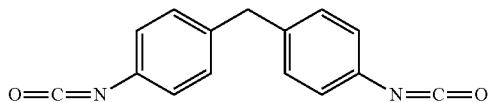 [SMILES: O=C=Nc1ccc(Cc2ccc(N=C=O)cc2)cc1]

or, if several diisocyanates are used, constitutes the predominant diisocyanate by weight, preferably representing, in the latter case, more than 50% of the total weight of the diisocyanate compounds.

Use may advantageously be made of a caprolactam-blocked 4,4'-MDI (for example the product in the solid form "Grilbond IL-6" from EMS), of formula:

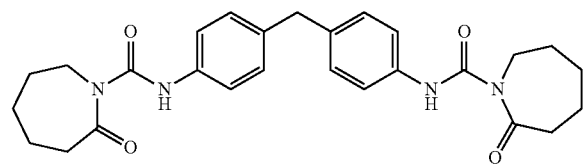 [SMILES: O=C1CCCCCN1C(=O)Nc1ccc(Cc2ccc(NC(=O)N3CCCCCC3=O)cc2)cc1]

As the use of the compound of the invention is not limited to the synthesis of a polyurea of the linear type (case of a diisocyanate), it might also be possible to use, in particular with the aim of increasing the Tg of the polymer by formation of a three-dimensional network, a triisocyanate compound, such as, for example, an MDI trimer having a triazine nucleus of formula:

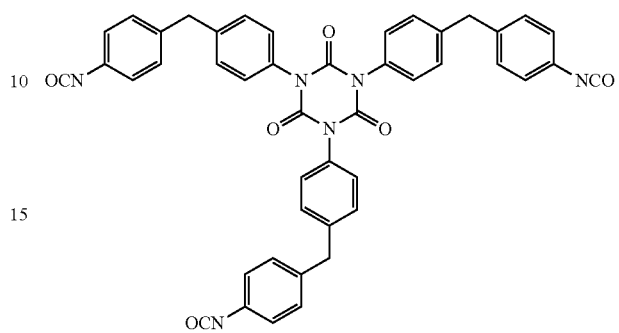

According to a preferred form of the invention, in the polyurea polymer resulting from the polyamine of the invention, the sulphur-comprising polyaromatic polyamine structural units derived from the said polyamine of the invention and the base structural units having urea (—NH—CO—NH—) units are connected to one another according to a sub-unit corresponding to the formula (IV) below:

—HN—Ar$_1$—NH—Y[X]$_n$—HN—Ar$_2$—NH—CO—NH—Z$_3$—NH—CO— in which:
  Ar$_1$, Ar$_2$, X, "n", "m" and Z$_1$ have the meanings given above;
  Y represents the string:

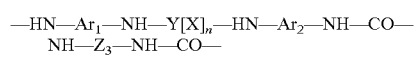

and Z$_3$ represents an aliphatic, cycloaliphatic or aromatic divalent bonding group, the aliphatic group preferably comprising from 1 to 30 (more preferably from 1 to 20) carbon atoms, the cycloaliphatic group preferably comprising from 3 to 30 (more preferably from 3 to 20) carbon atoms and the aromatic group comprising from 6 to 30 (more preferably from 6 to 20) carbon atoms.

The appended FIGS. 5 to 10 represent preferred examples of polyureas resulting from polyamines in accordance with the invention and also various possible schemes for the synthesis of these polyureas from these polyamines in accordance with the invention.

Figure 5:
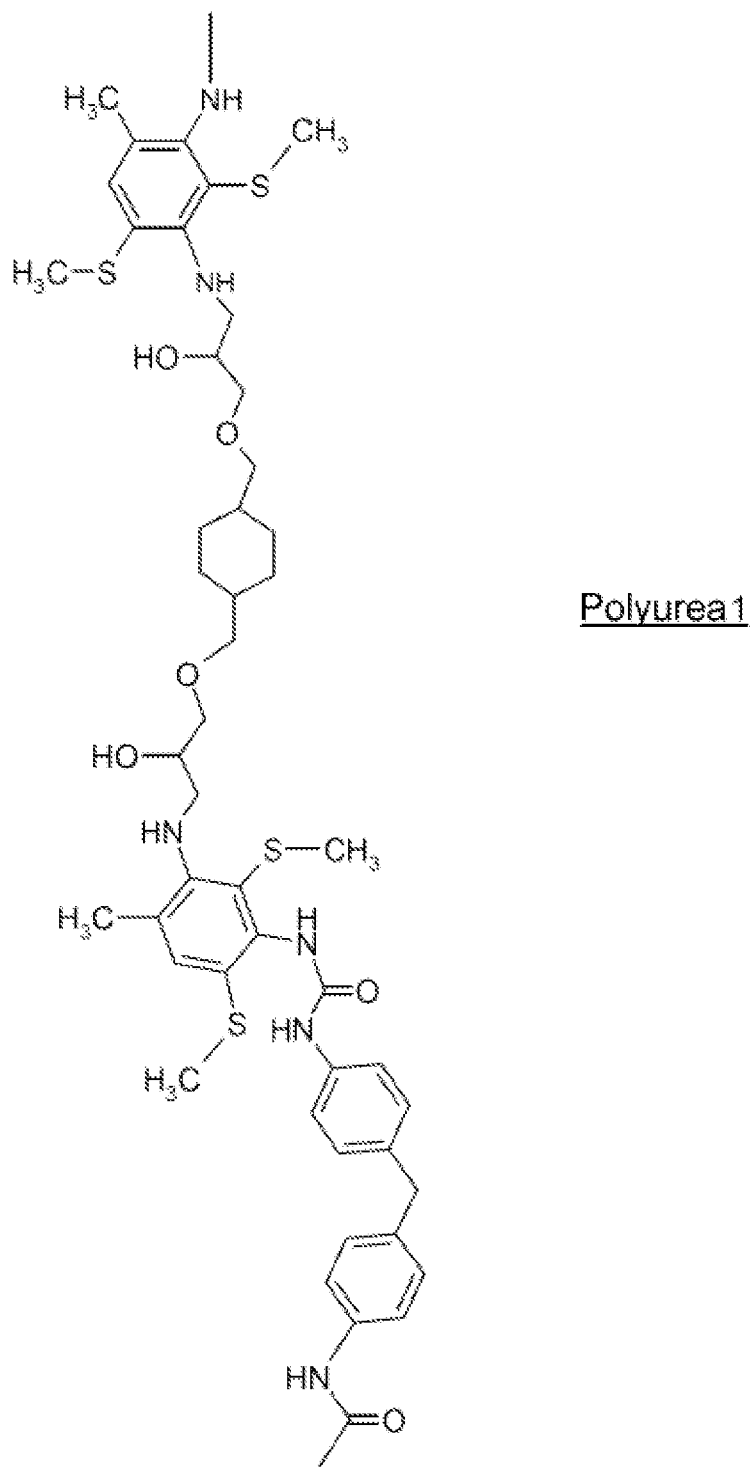
FIG. 5—an example of sequence (repeat structural unit) of a polymer (Polyurea 1), resulting from the reaction of a diisocyanate MDI (or MDI precursor) and of a polyamine in accordance with the invention (Prepolymer 1)

First of all, the appended FIG. 5 represents a string example of a polymer (hereinafter "Polyurea 1"), resulting from the reaction of a monomer MDI and a starting polyamine (hereinafter "Prepolymer 1") in accordance with the invention having the general formula:

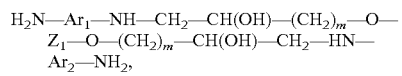

in which Ar$_1$, Ar$_2$ and Z$_1$ have the general definitions given above for the sub-units of formula (I) and more particularly the characteristics corresponding to the final sub-unit of formula (III-A), namely that the two amino (H$_2$N— and —NH) groups are in the meta position with respect to one another on each phenylene (Ar$_1$ and Ar$_2$) group, "m" is equal to 1 for each (CH$_2$)$_m$ group, "n" is equal to 0 and Z$_1$ is cyclohexane-1,4-dimethylene.

Figure 6:
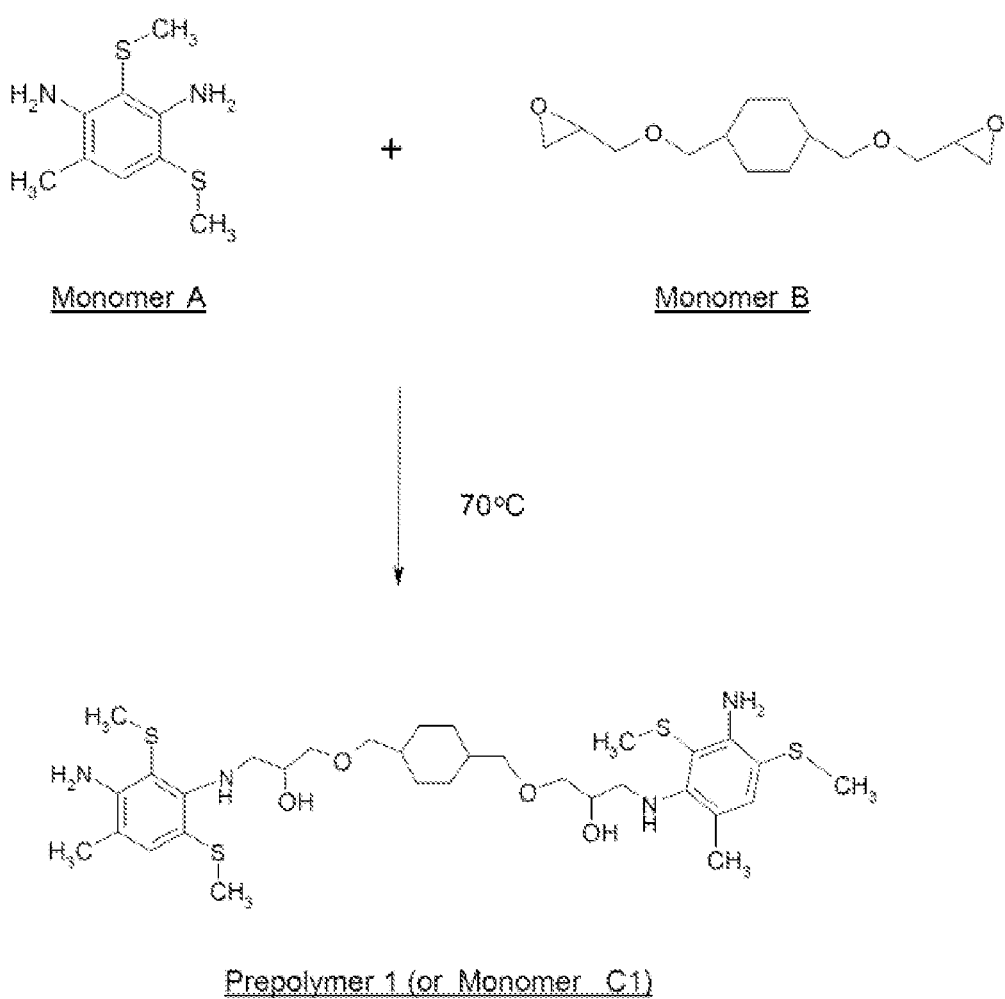
FIG. 6—a scheme for the possible synthesis, starting from two Monomers A and B, of a polyamine (Prepolymer 1, also known as Monomer C1) in accordance with the invention used in the preparation of the polymer Polyurea 1.
Figure 7:
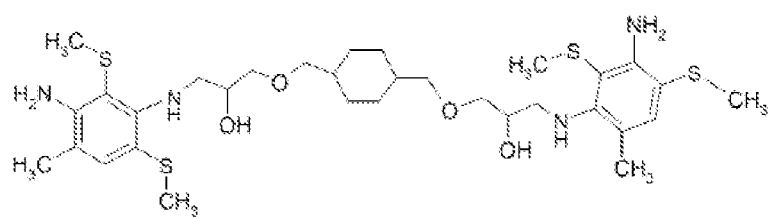
FIG. 7—a scheme for the possible synthesis of the polymer Polyurea 1 starting from the preceding polyamine (Monomer C1) in accordance with the invention and a blocked diisocyanate (MDI) (referred to as Monomer D)
Figure 7:
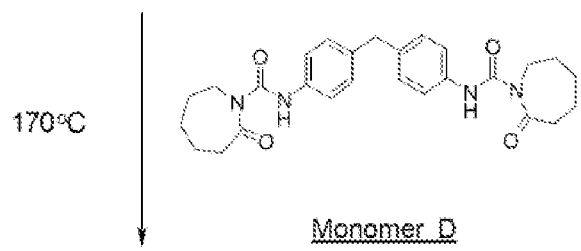
Figure 7:
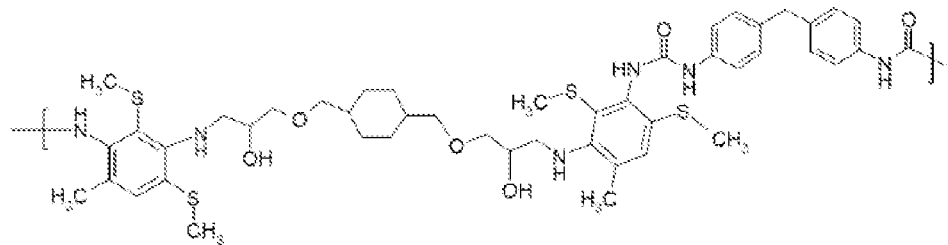

FIGS. 6 and 7 which follow illustrate examples of processes which can be used for the synthesis of Prepolymer 1 and Polyurea 1 respectively, which processes will be described in detail subsequently.

Figure 8:
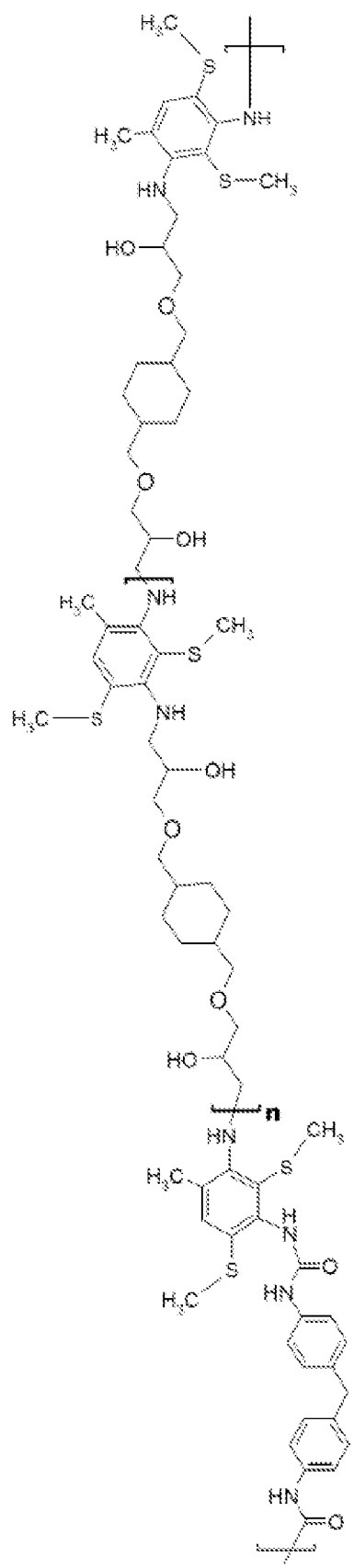
FIG. 8—an example of sequence (repeat structural unit) of another polyurea (Polyurea 2), resulting from the reaction of a diisocyanate MDI (or MDI precursor) and of a polyamine in accordance with the invention (Prepolymer 2)

The appended FIG. 8 represents another string example of a polymer ("Polyurea 2"), resulting from the reaction of a monomer MDI and another starting polyamine (hereinafter "Prepolymer 2") according to the invention having the general formula:

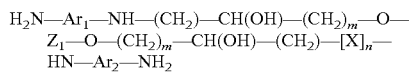

with X corresponding to the formula:

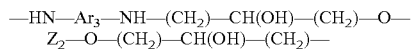

in which $Ar_1$, $Ar_2$, $Ar_3$, $Z_1$ and $Z_2$ have the general definitions given above for the sub-units of formula (I) and more particularly the characteristics corresponding to the final sub-unit of formula (III-B), namely that the two amino groups are in the meta position with respect to one another on each phenylene ($Ar_1$, $Ar_2$ and $Ar_3$) group, "m" is equal to 1 for each $(CH_2)_m$ group, "n" is equal to 1 and $Z_1$ and $Z_2$ represent cyclohexane-1,4-dimethylene.

Figure 9:
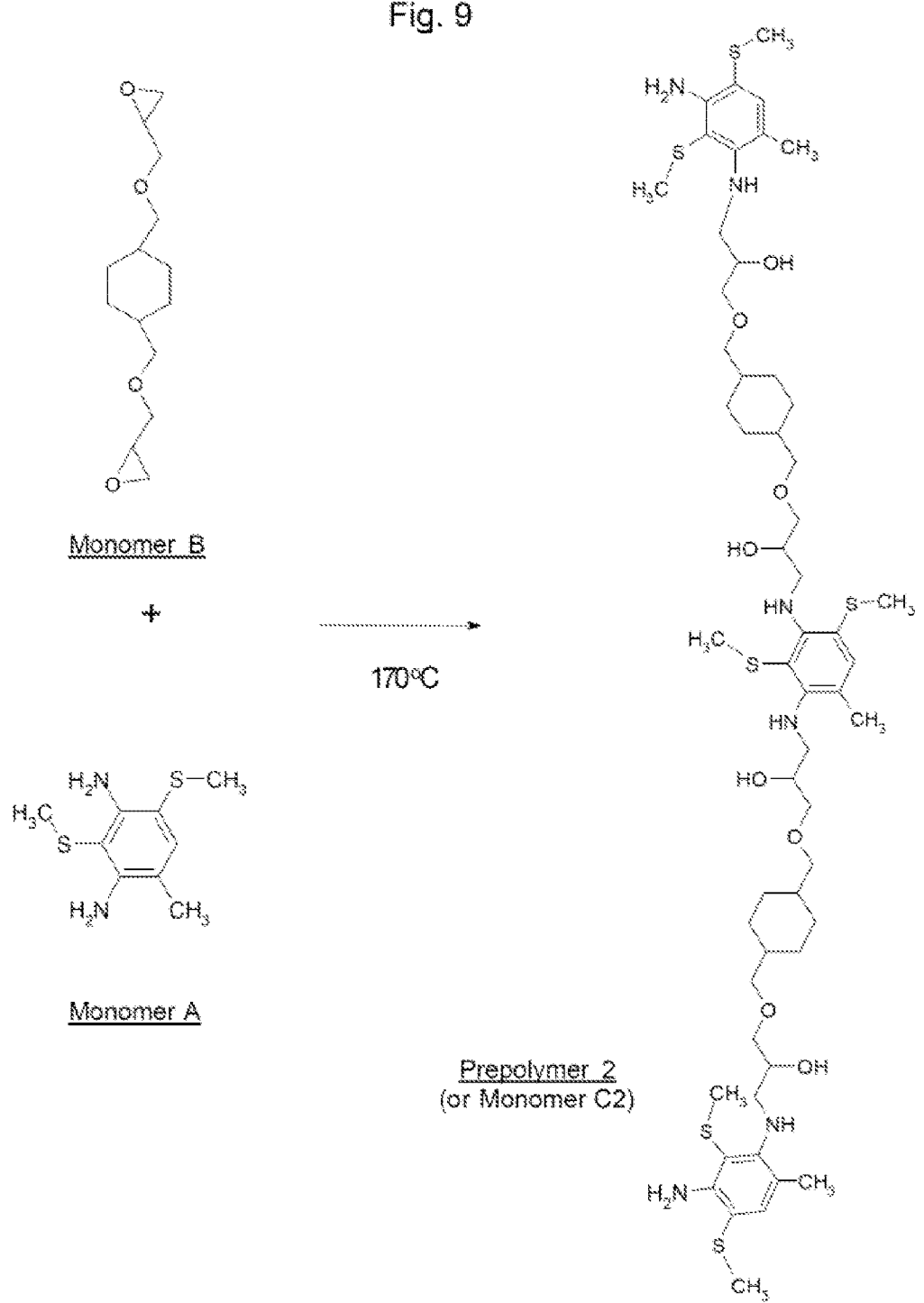
FIG. 9—a scheme for the possible synthesis, starting from two Monomers A and B, of a polyamine in accordance with the invention (Prepolymer 2 or Monomer C2) used in the preparation of the polymer Polyurea 2.
Figure 10:
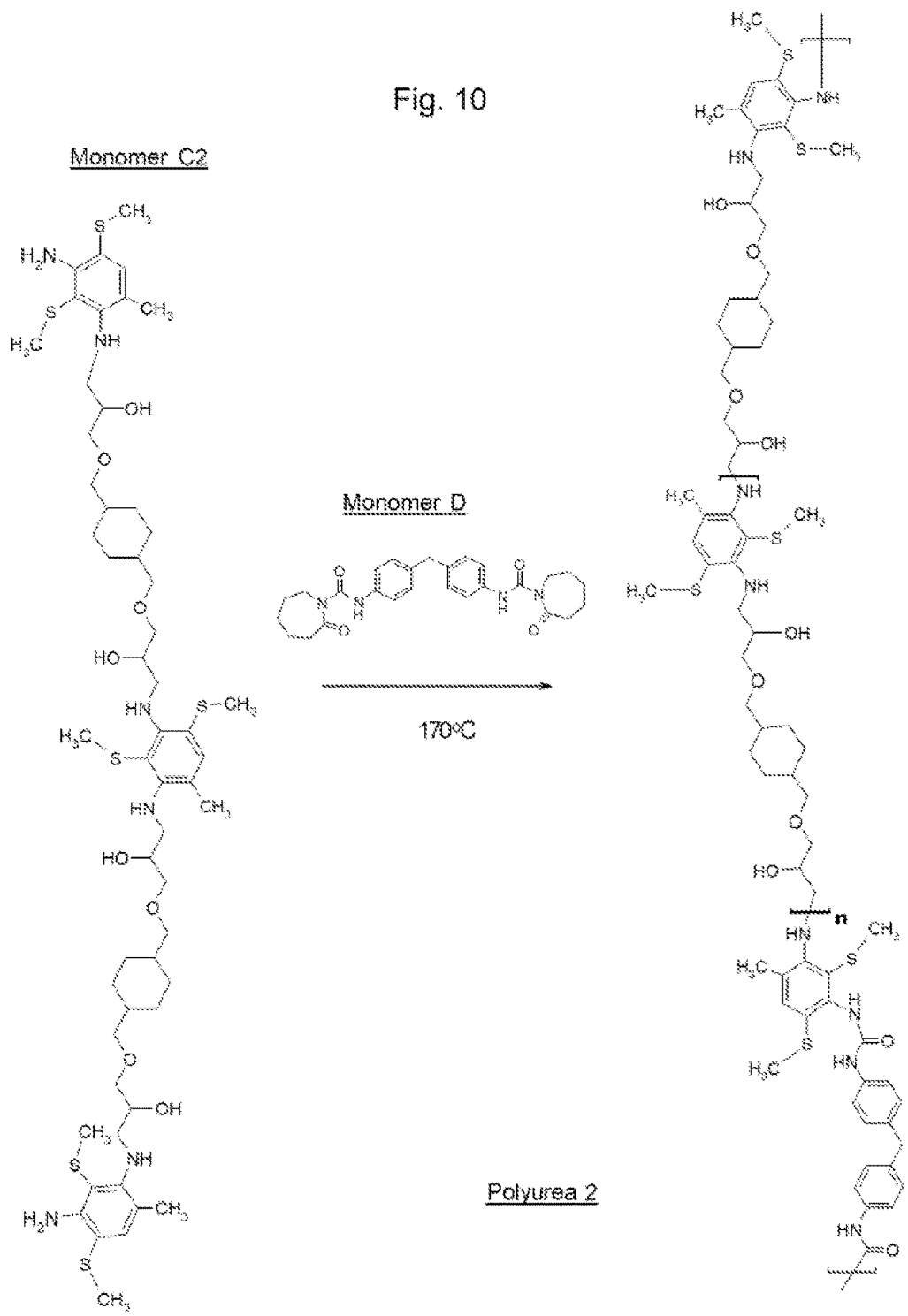
FIG. 10—a scheme for the possible synthesis of the polymer Polyurea 2 starting from the preceding polyamine (Monomer C2) in accordance with the invention and a blocked diisocyanate (MDI) (Monomer D).

FIGS. 9 and 10 which follow illustrate examples of processes which can be used for the synthesis of Prepolymer 2 and Polyurea 2 respectively, which processes will be described in detail subsequently.

The polyurea which can be synthesized from a polyamine compound in accordance with the invention exhibits a glass transition temperature Tg, measured by DSC (Differential Scanning Calorimetry), for example according to ASTM D3418, which is preferably greater than 50° C., more preferably greater than 100° C. and in particular of between 130° C. and 250° C.

As indicated above, this polyurea which can be synthesized from the polyamine in accordance with the invention can advantageously be used as hydrophobic coating on any type of substrate, in particular made of metal or glass, or also as adhesion primer on any type of metal reinforcer, such as, for example, a thread, a film, a plate or a cord made of carbon steel coated or not coated with brass, intended in particular to reinforce an unsaturated rubber matrix, such as natural rubber.

5. EXAMPLES OF THE IMPLEMENTATION OF THE INVENTION

In the present patent application, unless expressly indicated otherwise, all the percentages (%) shown are percentages by weight.

The tests which follow describe the synthesis of Prepolymers 1 and 2 in accordance with the invention, also denoted Monomers C1 and C2, from Monomer A and Monomer B, and then the syntheses of Polyureas 1, 2 and 3 from these Prepolymers 1 and 2 (Monomers C1 and C2) and from a Monomer D (MDI).

During these tests, various adhesion tests are carried out, on different substrates (glass or metal), in order to illustrate the excellent adhesive performance of the polyureas resulting from the polyamines in accordance with the invention.

5.1. Test 1—Preparation of Prepolymers 1 and 2 According to the Invention

Prepolymers 1 and 2 (also called Monomers C1 and C2), the respective formulae of which are given in FIGS. 6 and 9, were prepared from two Monomers A and B according to the procedures represented diagrammatically in FIGS. 6 and 9, as explained in detail below.

Monomer A is the product Ethacure 300 (supplier Albemarle, Belgium), available in the form of a relatively viscous liquid of brownish colour; it is composed to approximately 96% of a mixture of 3,5-bis(methylthio)-2,4-toluenediamine and 3,5-bis(methylthio)-2,6-toluenediamine isomers (ratio by weight of approximately 4/1 according to chromatographic analysis).

Monomer B is 1,4-cyclohexanedimethanol diglycidyl ether (abbreviated to "CHXDE") (supplier Aldrich, Switzerland), available in the form of a technical grade (approximately 61% of a mixture of cis/trans diepoxides). According to the technical data available (for example Patent Application U.S. 2011/0039982), CHXDE is a complex chemical mixture comprising the diepoxides (approximately 61%), residual cyclohexanedimethanol (approximately 2%), monoepoxides (approximately 8%) and, finally, polymeric epoxide entities (approximately 29%). According to the NMR analysis, the epoxide equivalent weight (EEW) of the compound used here is equal to approximately 159 (theoretical EEW equal to 128 in the case of a pure compound).

During a first stage, the two Monomers A and B above were first of all purified as follows.

The product Ethacure 300 (approximately 40 g) is deposited in a chromatography column (700 g of silica); a mixture of hexane/dichloromethane/ethyl acetate solvent (ratios 10:8:2) is used as mobile phase. The 2,4-toluenediamine isomer is eluted first, followed by the second 2,6-toluenediamine isomer. Under these conditions, the impurities (blue-green colour) are not eluted and can be easily separated from the targeted constituents.

The identification of the 2,4 and 2,6 isomers is confirmed by the $^1H$ NMR (500 MHz) analysis in the solvent $d_6$-DMSO, which gives the following results:

3,5-bis(methylthio)-2,4-toluenediamine:
   6.96 (s, 1H), 5.21-5.23 (d, 4H), 2.16 (s, 3H), 2.10 (s, 3H), 1.97 (s, 3H).

3,5-bis(methylthio)-2,6-toluenediamine
   7.22 (s, 1H), 5.09 (s, 4H), 2.15 (s, 6H), 1.92 (s, 3H).

For its part, the product "CHXDE" is isolated by vacuum distillation according to the experimental conditions described in Example 3 of the abovementioned document US 2011/0039982. The cis/trans structures of the diepoxide are confirmed by $^1H$ NMR analysis in $d_6$-DMSO.

After these purification stages, Prepolymers 1 and 2 in accordance with the invention were prepared as represented diagrammatically in FIGS. 6 and 9 respectively, according to the more detailed information which follows.

180 mg of Monomer B (0.702 mmol) and then 3 ml of tetrahydrofuran (THF) are placed in a predried (100° C. under vacuum) 25 ml three-necked round-bottomed flask equipped with a magnetic bar and a reflux condenser provided with circulation for nitrogen. 150 mg of Monomer A (i.e., 0.702 mmol) are then added with stirring. The mixture obtained is heated at reflux at 70° C. for one hour and then the THF is removed by distillation. The transparent liquid thus obtained (Prepolymer 1 or Monomer C1 in accordance with the invention) was analysed by DSC from −80° C. to 200° C.: the Tg measured (second pass) is equal to approximately −40° C.

Prepolymer 2 (Monomer C2) was prepared in a similar way starting from the same two compounds (150 mg of Monomer A and 180 mg of Monomer B), the mixture being heated at 170° C. for one and a half hours (without THF solvent) in a 25 ml round-bottomed flask equipped with a reflux condenser, the reaction being carried out under air. The reaction product thus obtained (Prepolymer 2 or Monomer C2 in accordance with the invention) exhibited a Tg of approximately +31° C. (second pass of DSC).

5.2. Test 2—Synthesis of Polyureas 1 and 2

In a final stage as represented diagrammatically in FIGS. 7 and 10 respectively, Polyureas 1 and 2 were then synthesized by reaction of Prepolymers 1 and 2 according to the invention with Monomer D (caprolactam-blocked MDI), as described in detail below.

330.5 mg of Monomer C1 (Prepolymer 1) and then 336 mg of Monomer D (Grilbond IL6) are placed in 8 ml of DTP (1,3-dimethyl-3,4,5,6-tetrahydro-2(1H)-pyrimidinone; CAS 7226-23-5) solvent in a glass vessel. The suspension is placed under mechanical vibration (vortex device) for a few seconds until Monomer D has completely dissolved.

1.5 ml of this solution are then uniformly deposited over a glass sheet (10×10 cm); the glass sheet is subsequently placed in an oven (ventilation under air) at 170° C. for 15 min, which stage is followed by 15 min at 190° C. under vacuum in order to remove the traces of solvent.

The thin layer of Polyurea 1 thus obtained displayed excellent adhesion to the glass (impossibility of separating by pulling the polymer from the glass). This Polyurea 1, analysed by DSC, exhibited a Tg of approximately 190° C. (second pass).

For the synthesis of Polyurea 2, Prepolymer 2 (Monomer C2, 0.702 mmol) was partially dissolved in 12 ml of DTP heated in a first step at approximately 110° C. for 2 min. Then, by heating the medium at 170° C. for 30 min, a highly soluble product is obtained. 336 mg of Monomer D (0.702 mmol) were subsequently added and everything was mixed in a stirrer (vortex device) until Monomer D had completely dissolved.

4 ml of the solution thus obtained were then uniformly deposited over a sheet made of zinc-coated steel (100 cm² surface area); everything was placed in an oven (ventilation under air) at 170° C. for 15 min. The transparent yellow film was subsequently treated under vacuum at 190° C. for 15 min in order to remove the traces of solvent.

The final Polyurea 2 thus obtained, in the form of a thin film, displayed excellent adhesion to the steel sheet (impossibility of separating by pulling the polymer from the metal). This Polyurea 2, analysed by DSC between −80° C. and +200° C. (according to a gradient of 10° C./min), exhibited a Tg of approximately 160° C. (second pass).

5.3. Test 3 Synthesis of Polyurea 3 and Metal/Rubber Composite Adhesion Tests

During an additional test, a new polymer (Polyurea 3) was synthesized by reaction in solution (DTP solvent) of Monomer C1 in accordance with the invention (Prepolymer 1, addition product of Monomers A and B, both used in this test in purified form) with solid MDI (in this instance in the non-blocked form, Sigma-Aldrich), according to the procedure which follows.

1.5 g of purified Monomer B (4$^{th}$ fraction) and then 20 ml of DTP solvent are added to a dry apparatus equipped with a 250 ml three-necked round-bottomed flask, with a reflux condenser, with a magnetic bar and with a nitrogen outlet. At the same time, a first solution of 1.5 g of 3,5-bis(methylthio)-2,4-toluenediamine (isolated from the product Ethacure 300) in 30 ml of DTP was prepared and placed in a dropping funnel and a second solution of 1.75 g of diphenylmethane diisocyanate (MDI) dissolved in 30 ml of DTP was prepared and placed in a second dropping funnel, everything under nitrogen.

The aromatic amine and MDI solutions were added dropwise with stirring and at 100° C. (internal temperature of the round-bottomed flask). The polymerization reaction was continued at 100° C. for 4 h, followed by a stage at 160° C. for 1 h.

The Polyurea 3 thus obtained, in the form of a transparent yellow solution, was analysed by DSC between −80° C. and +200° C. (according to a gradient of 10° C/min); it exhibited a Tg equal to approximately 150° C. (second pass).

This Polyurea 3 solution (0.1 ml) was then deposited over a strip made of brass-coated steel (steel with a carbon content equal to 1%) of dimensions 10 cm×0.5 cm×0.2 mm and then everything was placed in an oven at 175° C. (ventilation under air) for 15 min and then at 175° C. under vacuum for an additional 15 min in order to remove any trace of solvent.

The strip was subsequently cooled to ambient temperature and then 0.75 ml of a solution of epoxidized natural rubber (ENR, with a degree of epoxidation of 25%, supplier Aldrich) and diisocyanate (Suprasec 2020 liquid MDI from Huntsman) was deposited on the thin layer of polyurea film thus formed, which solution was prepared as follows: 150 mg of ENR were dissolved beforehand in 5 ml of toluene at 23° C. for 30 min with stirring (magnetic bar); 100 mg of diisocyanate were subsequently added under a stream of nitrogen. The strip thus prepared was finally treated in an oven at 100° C. under vacuum for 15 min.

The strip made of brass-coated steel thus coated with the film of Polyurea 3, itself covered with the thin layer of ENR, was subsequently placed in a conventional rubber composition for a belt reinforcement of a passenger vehicle tyre, based on natural rubber, on carbon black and silica as filler and on a vulcanization system (sulphur and sulphenamide accelerator), this composition being devoid of cobalt salt.

The metal/rubber composite test specimen thus prepared was then placed under a press and everything was cured (vulcanized) at 165° C. for 30 min under a pressure of 20 bar.

After vulcanization of the rubber, excellent adhesive bonding between the rubber matrix and the strip made of brass-coated steel was obtained, despite the absence of cobalt salt in the rubber matrix; this is because, during peel tests carried out both at ambient temperature (23° C.) and at high temperature (100° C.), it was found that the failure occurred systematically in the rubber matrix itself and not at the interphase between metal and rubber.

In conclusion, the sulphur-comprising polyaromatic polyamines of the invention make it possible to synthesize polyureas which are characterized by a high glass transition temperature, a high thermal and chemical stability and an excellent adhesion to glass or metal.

By virtue of the invention, these polyureas, used as adhesion primer on metal in metal/rubber composites, make it possible very advantageously to subsequently adhesively bond the metal to the rubber matrices using simple textile adhesives, such as "RFL" (resorcinol/formaldehyde latex) adhesives or other equivalent adhesive compositions, or also to directly (that is to say, without employing such adhesives) to these rubber matrices when the latter comprise, for example, appropriate functionalized unsaturated elastomers, such as epoxidized elastomers.

Thus, the cobalt salts (or other metal salts) can in particular be dispensed with in the rubber compositions intended to be connected to brass-coated metal reinforcers.

The invention claimed is:

1. A sulfur-comprising polyaromatic polyamine compound corresponding to the formula (I):

H₂N—Ar₁—NH—CH₂—CH(OH)—(CH₂)ₘ—O—
Z₁—O—(CH₂)ₘ—CH(OH)—CH₂—[X]ₙ—
HN—Ar₂—NH₂ wherein X represents the string:

—HN—Ar₃—NH—(CH₂)—CH(OH)—(CH₂)ₘ—
O—Z₂—O—(CH₂)ₘ—CH(OH)—(CH₂)—;

wherein n represents an integer equal to zero or different from zero;

wherein m, which are identical or different, represent an integer within a range from 1 to 10;

wherein Z₁ and Z₂ represent cyclohexane-1,4-dimethylene;

wherein Ar₁, Ar₂ and Ar₃, which are identical or different, each represent a phenylene group, at least one of these phenylene groups bearing one, two, three or four groups of formula —Sₓ—R in which x is an integer from 1 to 8 and R represents hydrogen or a hydrocarbon group which optionally comprises a heteroatom and which comprises from 1 to 10 carbon atoms.

2. The compound according to claim 1, wherein n is equal to 1.

3. The compound according to claim 1, wherein n is within a range from 2 to 20.

4. The compound according to claim 3, wherein n is within a range from 2 to 10.

5. The compound according to claim 1, wherein m, which are identical or different, represent an integer within a range from 1 to 5.

6. The compound according to claim 5, wherein m, which are identical or different, represent an integer equal to 1 or 2.

7. The compound according to claim 6, wherein m is preferably equal to 1.

8. The compound according to claim 1, wherein each of the Ar₁, Ar₂ and Ar₃ groups bears one, two, three or four groups of formula —Sₓ—R.

9. The compound according to claim 1, wherein x is within a range from 1 to 4.

10. The compound according to claim 9, wherein x is equal to 1 or 2.

11. The compound according to claim 1, wherein R is an alkyl.

12. The compound according to claim 11, wherein R is an alkyl having from 1 to 5 carbon atoms.

13. The compound according to claim 12, wherein R represents a methyl or an ethyl.

14. The compound according to claim 13, wherein R is a methyl.

15. The compound according to claim 1, wherein the monovalent phenylenediamino strings H₂N—Ar₁—NH— and —HN—Ar₂—NH₂, which are identical or different, correspond to one of the formulae (III-a), (III-b) and (III-c):

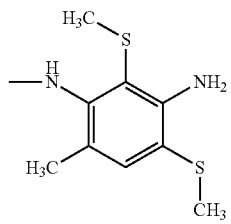
(III-a)

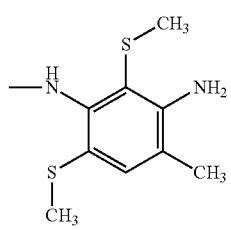
(III-b)

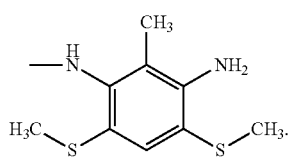
(III-c)

16. The compound according to claim 1, wherein the divalent phenylenediamino strings —HN—Ar₃—NH—, which are identical or different, correspond to either of the formulae (III-d) and (III-e):

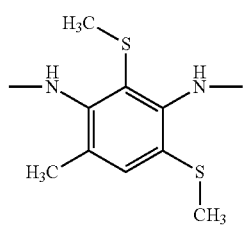
(III-d)

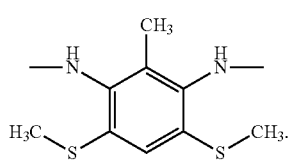
(III-e)

17. A polyurea made using at least one sulfur-comprising polyaromatic polyamine compound according to claim 1.

18. A process for the synthesis of a polyurea comprising the step of:
polycondensating at least one sulfur-comprising polyaromatic polyamine compound according to claim 1 with a polyisocyanate compound.

19. A process for the synthesis of a polyurea comprising the step of:
using a sulfur-comprising polyaromatic polyamine compound according to claim 1.

* * * * *